United States Patent [19]

Kapralis et al.

[11] 4,379,448
[45] Apr. 12, 1983

[54] TRIGGER TO INITIATE CRYSTALLIZATION

[76] Inventors: Imants P. Kapralis, 3020 S. Punta Del Este Dr., Hacienda Heights, Calif. 91745; Harry Krukle, 7023 Bevis Ave., Van Nuys, Calif. 91405

[21] Appl. No.: 350,564

[22] Filed: Feb. 22, 1982

Related U.S. Application Data

[63] Continuation of Ser. No. 113,356, Jan. 18, 1980, abandoned.

[51] Int. Cl.³ .................................................. F24J 1/00
[52] U.S. Cl. ................................................... 126/263
[58] Field of Search .............. 126/263, 400; 62/4; 44/3 R, 3 A, 3 B, 3 C; 165/104 S, DIG. 4; 23/300, 301 R; 156/621; 252/70; 220/305

[56] References Cited

U.S. PATENT DOCUMENTS

| | | |
|---|---|---|
| 811,750 | 2/1906 | Spieske . |
| 1,502,744 | 7/1924 | Perrault . |
| 1,656,366 | 1/1928 | Sterling et al. . |
| 1,679,432 | 8/1928 | Lyon . |
| 1,894,775 | 1/1933 | Levenson . |
| 2,157,169 | 5/1939 | Foster . |
| 2,220,777 | 11/1940 | Othmer ........................ 126/263 X |
| 2,827,438 | 3/1958 | Broadley et al. . |
| 3,175,558 | 3/1965 | Caillouette et al. . |
| 3,223,081 | 12/1965 | Hunt . |
| 3,475,239 | 10/1969 | Fearon et al. . |
| 3,536,058 | 10/1970 | Hearst et al. ..................... 126/204 |
| 3,550,578 | 12/1970 | Fearon et al. ..................... 126/263 |
| 3,854,156 | 12/1974 | Williams ............................. 5/347 |
| 3,951,127 | 4/1976 | Watson et al. ..................... 126/206 |
| 4,077,390 | 3/1978 | Stanley et al. ..................... 126/263 |
| 4,126,758 | 11/1978 | Krumme ........................ 174/52 FP |

Primary Examiner—Samuel Scott
Assistant Examiner—Randall L. Green
Attorney, Agent, or Firm—William W. Haefliger

[57] ABSTRACT

A trigger to initiate crystallization of a supercoated salt solution comprises, (a) a thin strip having a perimeter,
(b) said strip having a multiplicity of slits formed therein, each slit characterized as having opposed elongated edges which face one another in near touching relation,
(c) the strip further characterized as having two configurations between which it is bendable with snap-displacement causing the slit edges to initiate progressive exothermic crystallization of said salt in the solution.

3 Claims, 9 Drawing Figures

U.S. Patent Apr. 12, 1983 4,379,448
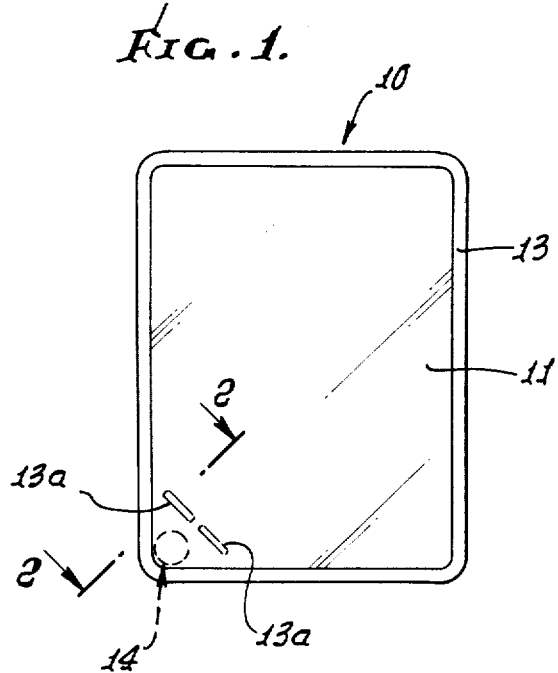
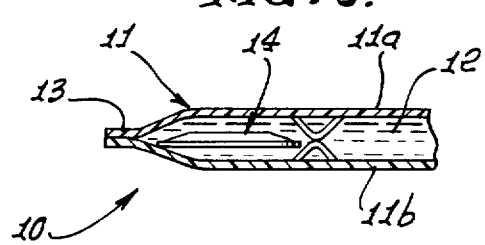
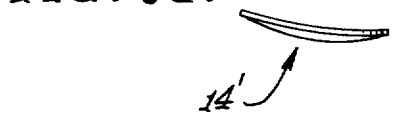
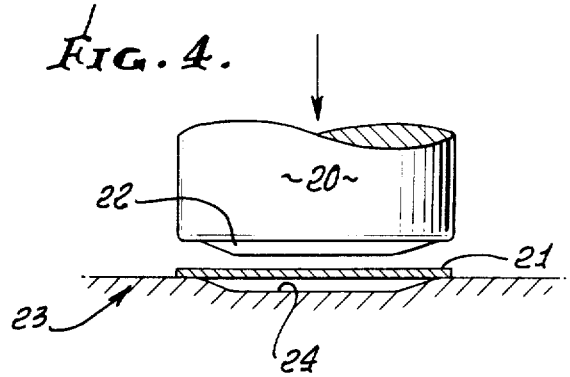
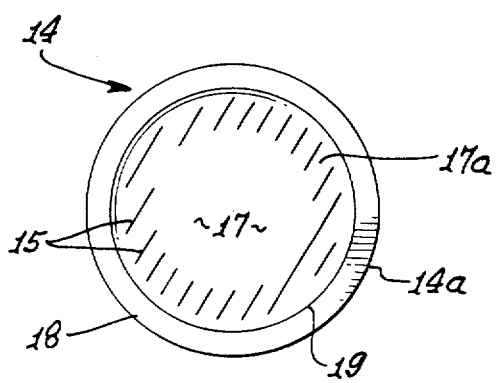
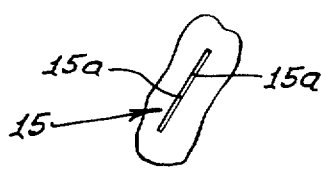
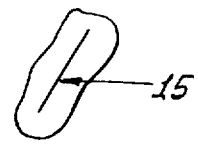
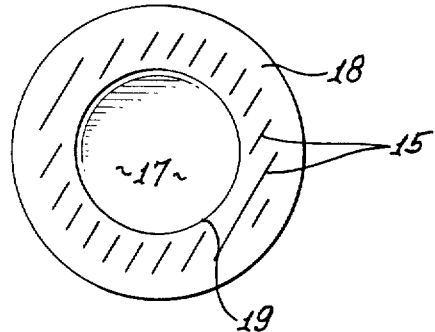
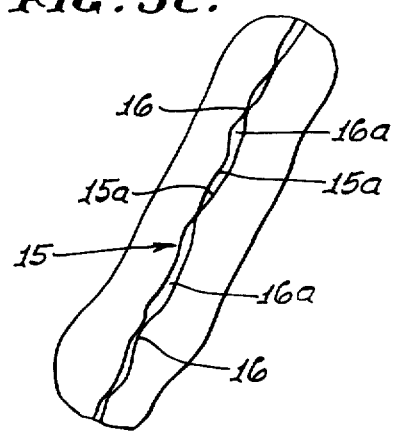

4,379,448

TRIGGER TO INITIATE CRYSTALLIZATION

This is a continuation of application Ser. No. 113,356, filed Jan. 18, 1980 and abandoned.

BACKGROUND OF THE INVENTION

This invention relates generally to the initiation of crystallization of a supercooled salt solution; more particularly it concerns the provision of a highly advantageous trigger that is easily deformable and is constructed to initiate such crystallation when the trigger is deformed, and without failure or injury to a plastic container in which the trigger is confined.

Devices of the general type with which the present invention is concerned are described in U.S. Pat. No. 4,077,390; however, such devices have tended to suffer from unreliable triggering of crystallization. For example, flexing of the actuator strips described in that patent at times will initiate crystallization and at other times will not. This greatly aggravates the user and reduces the practicality and utility of such devices.

SUMMARY OF THE INVENTION

It is a major object of the present invention to provide an improved trigger which will reliably and repeatedly produce or initiate crystallization of supercooled solutions; which is readily produced; and which will not injure or tear the plastic container in which it is incorporated. Fundamentally, the trigger comprises:

(a) a thin strip having a perimeter, (b) said strip having a multiplicity of slits formed therein, each slit characterized as having opposed elongated edges which face one another in near touching relation, (c) the strip further characterized as having two configurations between which it is bendable with snap-displacement causing the slit edges to initiate progressive exothermic crystallization of said salt in the solution.

As will appear, portions of the opposed edges of the slits typically touch one another, so that they may rub against one another and compress the solution trapped between those edges when the trigger is snap-deformed; the trigger is typically formed as a disc wherein the slits are spaced inwardly from the boundary or periphery of the disc; the disc typically has a dished central portion free of slits and adapted to "oil can" or snap "over center" when the disc is subjected to flexing or bending; and the metal of the edges adjacent the slits is impacted during fabrication to impact orient the molecular structure so as to aid the functioning of the disc to produce or initiate crystallization.

These and other objects and advantages of the invention, as well as the details of an illustrative embodiment, will be more fully understood from the following description and drawings, in which:

DRAWING DESCRIPTION

FIG. 1 is a plan view of a device incorporating the invention;

FIG. 2 is an enlarged section taken on lines 2—2 of FIG. 1, and showing a trigger in one side elevation configuration;

FIG. 2a is a side elevation showing the FIG. 2 trigger in a second side elevation configuration, i.e. after snap-displacement;

FIG. 3 is a further enlarged plan view of the trigger seen in FIG. 2;

FIG. 4 is a side elevation showing a step in the fabrication of the FIGS. 2 and 3 trigger;

FIG. 5a is a fragmentary plan view of a slit as initially formed in the trigger blank or strip;

FIG. 5b is a fragmentary plan view like FIG. 5a, but showing the slit after impacting as in FIG. 4; and FIG. 5c is an enlarged view of the slit, FIG. 6 is a view like FIG. 3, showing a modified trigger.

DETAILED DESCRIPTION

Referring first to FIGS. 1 and 2, a flexible heat pack 10 includes a flexible plastic container 11 containing a supercooled solution 12, one example being aqueous sodium acetate as referred to in U.S. Pat. No. 4,077,390. The container may consist of translucent or transparent plastic, such as polyethylene or PVC. The upper and lower container walls 11a and 11b may be peripherally bonded or heat sealed together, as indicated at 13, whereby the solution 12 is contained against leakage.

Located in the container is a trigger 14 adapted to be deformed to initiate exothermic crystallization of the salt in the solution, and for that purpose the concentration of the salt is sufficient to produce such crystallization in response to trigger bending, as will be described. The trigger may be retained in the corner of the rectangular container by interruptedly bonded portions of the container walls, indicated at 13a, inwardly of peripheral bonding 13; at the same time, the solution has access to the trigger, at all times, via interruptions between bonded portions 13a.

Generally speaking, the trigger comprises a thin strip, such as a metallic disc, having a perimeter indicated at 14a in FIG. 3. That perimeter is free of sharp edges that could injure or penetrate the plastic walls 11a and 11b. The strip has a multiplicity of slits 15 formed therein, each slit characterized as having opposed elongated edges which face one another in near touching relation. FIG. 5a shows a typical slit 15 as initially formed through the disc, and with opposite elongated edges 15a. FIG. 5b shows the slit as it finally is formed or exists, with the edges 15a so close together that they do not appear distinct; however, there are slight gaps between and spaced along such edges, which may touch one another between the gaps. Note for example the greatly enlarged slit 15 in FIG. 5c with edges 15a touching at points 16, and with gaps 16a between the edges. FIG. 5c is representative only, and the configurations of the edges 15a may vary, i.e. they may be less jagged for example.

The disc shaped strip 14 is characterized as having two configurations between which it is bendable with snap-displacement causing the slit edges to initiate progressive exothermic crystallization of the salt in the supercooled solution in the container. Note for example the first stable configuration of the trigger strip 14 in FIG. 2, and its second (and relatively stable) curved configuration 14' in FIG. 2a. The user simply applies finger pressure on the container walls 11a and 11b snap-deforms the disc 14 to FIG. 2a configuration, in the container. This causes the edges 15a of the slit to actuate the crystallation, due to sudden deformation (as for example sudden local compression) of the solution trapped or confined in the slit between the approximately touching edges 15a. The snap-displacement of the nearly touching edges is found to initiate crystallation without failure or malfunction.

These purposes are served to unusual advantage by causing the disc to have dished configuration as in FIG. 2, so as to "oil-can" when deformed, i.e. easily snap over-center into FIG. 2a configuration. Further, the disc has a central portion 17 free of slits, and an outermost annular portion. The latter contains the slits, which are typically spaced inwardly from the perimeter 14a so that the latter is continuous, aiding the snap-displacement referred to. In FIGS. 2, 2a and 3, the slits are located in the outermost annular section 17a of the dished portion of the disc; whereas in FIG. 6, the slits are located in the undished outer annular portion 18. Circles 19 in FIGS. 3 and 6 generally designate the boundary between the dished and undished portions.

Finally, the performance of the disc shaped strip to initiate crystallization is aided by impact orientation of the molecular structure of the edges 15a. FIG. 4 shows a striker 20 being forcibly urged downwardly toward blank 21, after the latter has had slits formed therein with spaced apart edges as in FIG. 5a. The bottom of the striker is protuberant at 22 to "dish" the blank (i.e. permanently deform it to have a central bulge as in FIG. 2); thereafter, the trigger disc is stamped or cut out of the blank by a suitable die. Back up platen 23 in FIG. 4 has a recess 24 to receive the deformed bulge of the blank 21.

We claim:

1. For use in initiating crystallization of a supercooled salt solution, the combination that includes a flexible container containing said solution, and a trigger located in the container in contact with the solution, said trigger comprising
   (a) a thin strip having a perimeter,
   (b) said strip having a multiplicity of generally parallel slits formed therein, each slit characterized as having opposed elongated edges which face one another in near touching relation,
   (c) the strip further characterized as having two configurations between which it is bendable with snap-displacement causing the slit edges to initiate progressive exothermic crystallization of said salt in the solution,
   (d) the strip being in the general form of a dished disc having a central portion and an outer portion surrounding said central portion, the outer portion having a curved periphery,
   (e) said slits confined to said outer portion and said central portion being free of said slits, said slits everywhere spaced inwardly from the disc periphery and located in an annular zone extending about said central portion, the slits defining a sector shaped portion of the annular zone located at a side of said central portion, whereby said periphery is free of slit edges which could otherwise penetrate the container, the container consisting of plastic material,
   (f) the strip consisting of metal and having molecular structure which is impact oriented.

2. The combination of claim 1 wherein said trigger is located in a corner of the container.

3. The combination of claim 2 including means confining the trigger in said corner.